United States Patent
Zhang et al.

(10) Patent No.: US 10,869,673 B2
(45) Date of Patent: Dec. 22, 2020

(54) EMBOLIC COIL WITH KICK-IN TAIL

(71) Applicant: Boston Scientific Scimed, Inc., Maple Grove, MN (US)

(72) Inventors: Ken Zhang, Maple Grove, MN (US); Gary Pederson, Albertville, MN (US); Katherine Routh, Coon Rapids, MN (US); Jeffry Johnson, Crystal, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 782 days.

(21) Appl. No.: 15/015,820

(22) Filed: Feb. 4, 2016

(65) Prior Publication Data

US 2016/0228127 A1 Aug. 11, 2016

Related U.S. Application Data

(60) Provisional application No. 62/112,384, filed on Feb. 5, 2015.

(51) Int. Cl.
*A61B 17/12* (2006.01)
*A61B 17/00* (2006.01)

(52) U.S. Cl.
CPC ............. *A61B 17/12145* (2013.01); *A61B 2017/00526* (2013.01); *A61B 2017/00867* (2013.01)

(58) Field of Classification Search
CPC .......... A61B 17/12145; A61B 17/1215; A61B 17/12154; A61B 17/1214; A61B 17/12131; A61B 17/12022; A61B 17/12027; A61B 17/12113; A61B 17/12118; A61B 17/12099; A61B 17/1204; A61B 17/12109; A61B 2017/1205; A61B 2017/12054
See application file for complete search history.

(56) References Cited

U.S. PATENT DOCUMENTS

| | | | | |
|---|---|---|---|---|
| 5,261,916 A | * | 11/1993 | Engelson | A61B 17/12022 606/108 |
| 5,649,949 A | * | 7/1997 | Wallace | A61B 17/12022 600/200 |
| 5,749,891 A | * | 5/1998 | Ken | A61B 17/12022 606/200 |
| 8,152,839 B2 | | 4/2012 | Bruiser et al. | |
| 8,425,550 B2 | | 4/2013 | Elliott et al. | |
| 2007/0141099 A1 | | 6/2007 | Buiser et al. | |
| 2009/0149864 A1 | | 6/2009 | Porter | |
| 2011/0245861 A1 | | 10/2011 | Chen et al. | |
| 2013/0190801 A1 | * | 7/2013 | Divino | A61B 17/12031 606/200 |

* cited by examiner

*Primary Examiner* — Diane D Yabut
(74) *Attorney, Agent, or Firm* — Kacvinsky Daisak Bluni PLLC

(57) ABSTRACT

The present disclosure relates to embolic coils that eliminate kick-back into a parent vessel by providing a proximal end that retracts following deployment within the vasculature. Also disclosed are methods of making such coils, delivery systems that comprise such coils, and methods of delivering such coils to a patient.

17 Claims, 5 Drawing Sheets ated within the site. One
EMBOLIC COIL WITH KICK-IN TAIL

RELATED APPLICATION INFORMATION

This application claims priority to and the benefit of, U.S. patent application Ser. No. 62/112,384, filed on Feb. 5, 2015, which is incorporated by reference in its entirety.

FIELD

The present disclosure relates to the field of embolic coils. More particularly, the present disclosure relates to embolic coils that address kick-back into the parent vessel by providing a proximal end that retracts following deployment within the vasculature.

BACKGROUND

Embolic coils are used for a variety of medical applications, including treatment of intra-vascular aneurysms. A common embolic coil takes the form of a soft, helically wound coil formed by winding a platinum (or platinum alloy) wire strand about a primary mandrel. The relative stiffness of the coil depends, among other things, on its composition, the diameter of the wire strand, the diameter of the primary mandrel, and the pitch of the primary windings. The coil is then wrapped around a larger, secondary mandrel, and heated to impart a secondary shape. For example, U.S. Pat. No. 4,994,069, issued to Ritchart et al., describes an embolic coil that assumes a linear, helical primary shape when stretched for placement through the lumen of a delivery catheter, and a folded, convoluted secondary shape when released from the delivery catheter and deposited in the vasculature.

Embolic coils are typically delivered to a selected site (e.g., aneurysm) within the vasculature using a delivery catheter in a minimally invasive procedure. To achieve an adequate density for embolus formation, it is common for multiple embolic coils to be implanted within the site. One issue with some existing embolic coils is the tendency of the proximal end of the coil to protrude out of the aneurysm into the parent vessel after being released from the delivery catheter. This phenomenon, referred to as kick-out or kick-back, has the potential to cause disruption of blood flow in the parent vessel that can lead to thrombosis.

The present disclosure is directed to embolic coils that address kick-back by providing a proximal end (also referred to herein as a "tail") that retracts following deployment within the vasculature.

SUMMARY

The present disclosure, in its various aspects, addresses an ongoing need in the field of embolization for accurate placement of embolic coils within a body lumen of a patient without a significant portion of the embolic coil extending into to the parent vasculature.

In accordance with some aspects, the present disclosure provides an embolic coil comprising an elongate helical primary shape having a diameter, a first end (also referred to herein as a proximal end) and a second end (also referred to herein as a distal end), wherein the primary shape is formed into a secondary shape in which a free energy state of the secondary shape (also referred to herein as the "free energy secondary shape") is a three-dimensional shape (e.g., a cone, dual cone, cylinder, sphere, cube, etc.) that defines a volume and comprises a bend in the first end of the primary shape.

In this regard, as seen from the description following and various drawings herein, the secondary shape need not fully enclose the volume. As used herein, an "end" of the coil is that portion of the coil that is adjacent a tip of the coil. In certain embodiments, the first end of the coil (which comprises the bend) may correspond to a portion of the coil ranging up to 20% of the total length of the coil, a portion of the coil ranging up to 15% of the total length of the coil, a portion of the coil ranging up to 10% of the total length of the coil, a portion of the coil ranging up to 5% of the total length of the coil, or a portion of the coil ranging up to 2.5% of the total length of the coil.

In various embodiments, which may be used in combination with any of the above aspects, a bending radius of the first end is less than five times the diameter of the elongate helical primary shape when the coil is in the free energy state.

In various embodiments, which may be used in combination with any of the above aspects and embodiments, the greatest width of the volume is greater than a bending radius of the first end, for example, ranging from 2 to 5 to 10 to 25 to 50 times the bending radius of the first end (by which is meant ranging between any two of the preceding numerical values, specifically, ranging from 2 to 50 times the bending radius of the first end, ranging from 2 to 25 times the bending radius of the first end, ranging 2 to 10 times the bending radius of the first end, ranging from 2 to 5 times the bending radius of the first end, ranging from 5 to 50 times the bending radius of the first end, ranging from 5 to 25 times the bending radius of the first end, ranging from 5 to 10 times the bending radius of the first end, ranging from 10 to 50 times the bending radius of the first end, ranging from 10 to 25 times the bending radius of the first end, or ranging from 25 to 50 times the bending radius of the first end).

In various embodiments, which may be used in combination with any of the above aspects and embodiments, the first end bends at an angle greater than 360 degrees when the coil is in the free energy state.

In various embodiments, which may be used in combination with any of the above aspects and embodiments, the first end comprises a two-dimensional spiral or a three-dimensional spiral when the coil is in the free energy state.

In various embodiments, which may be used in combination with any of the above aspects and embodiments, the first end of the primary shape bends at least partially back into the volume when the coil is in the free energy state. In preferred embodiments, at least a tip of the first end of the primary shape is positioned in the volume when the coil is in the free energy state. In some of these embodiments, a two-dimensional spiral or a three-dimensional spiral of the first end may be disposed entirely within the volume when the coil is in the free energy state.

In various embodiments, which may be used in combination with any of the above aspects and embodiments, the secondary shape defines a lumen therethrough, and the first end of the primary shape is at least partially disposed within the lumen when the coil is in the free energy state. For example, the secondary shape may be substantially in the form of a cylinder which forms the lumen, or the secondary shape may be substantially in the form of a single or dual cone which forms the lumen, among other possibilities. In some of these embodiments, a two-dimensional spiral or a three-dimensional spiral of the first end may be disposed entirely within the lumen when the coil is in the free energy state.

In various embodiments, which may be used in combination with any of the above aspects and embodiments, the bend is such that a tip of the first end points in a direction of the volume.

In various embodiments, which may be used in combination with any of the above aspects and embodiments, the first end bends at an angle greater than 60 degrees and less than 225 degrees, e.g., between 90 degrees and 180 degrees in some embodiments, when the coil is in the free energy state.

In various embodiments, which may be used in combination with any of the above aspects and embodiments, the secondary shape has a secondary axis, and an axis of the primary shape at the tip of the first end is within 45 degrees (beneficially within 30 degrees, more beneficially within 15 degrees) of parallel to the secondary axis.

In various embodiments, which may be used in combination with any of the above aspects and embodiments, the volume may be a single conic volume, a dual conic volume, or a cylindrical volume, a spherical volume, or a cubic volume, among other possible volume shapes.

In various embodiments, which may be used in combination with any of the above aspects and embodiments, the first end of the elongate helical primary shape is provided with an attachment feature. For example, the first end may be provided with an electrolytically dissolvable region or may be provided with a mechanical attachment feature that is configured to temporarily interlock with another component such as a delivery wire.

In various embodiments, which may be used in combination with any of the above aspects and embodiments, the embolic coil may be loaded into a delivery sheath.

Other aspects of the present disclosure pertain to delivery systems comprising (a) an embolic coil in accordance with any of the above aspects and embodiments and (b) a delivery wire that is temporarily attached to the embolic coil via an attachment feature. For example, the delivery wire may be detachably connected to the embolic coil via an attachment feature such as an electrolytically dissolvable attachment feature or a mechanical attachment feature, first instance, via a first attachment member on the embolic coil that temporarily interlocks with a second attachment member on the delivery wire (e.g., first and second interlocking attachment members such as first and second threaded members, first and second interlocking arms, etc.).

Other aspects of the present disclosure pertain to methods of embolic coil delivery that comprise (a) advancing an embolic coil of a delivery system in accordance with any of the above aspects and embodiments to a target occlusion area in a patient, and (b) releasing the embolic coil.

Still other aspects of the present disclosure pertain to methods of making an embolic coil (e.g., an embolic coil in accordance with any of the above aspects and embodiments). The methods comprise wrapping an elongate helical primary shape having a diameter, a first end and a second end around a first mandrel and disposing the first end in an interior of the first mandrel, thereby forming a secondary shape, and heating the elongate helical primary shape for a time and temperature sufficient to memorize the secondary shape.

In various embodiments, which may be used in combination with any of the above aspects, the first end may be inserted into a channel formed extending into the interior of the first mandrel (e.g., a straight or curved channel) or the first end may be wrapped around a smaller second mandrel that is disposed within the interior of the first mandrel (e.g., a cylindrical second mandrel or a conic second mandrel).

Other aspects of the present disclosure pertain to embolic coils formed by these methods.

These and other aspects, features, and advantages of the present disclosure will become immediately apparent to those of ordinary skill in the art upon review of the detailed description and claims to follow.

DRAWINGS

Non-limiting embodiments of the present disclosure will be described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure.

Figure 3A:
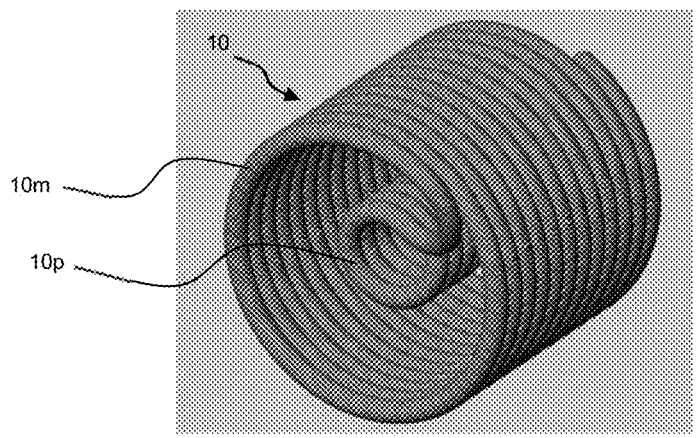

FIG. 3A provides a perspective view of an embodiment of an embolic coil with a kick-in tail, in accordance with the present disclosure.

Figure 3B:
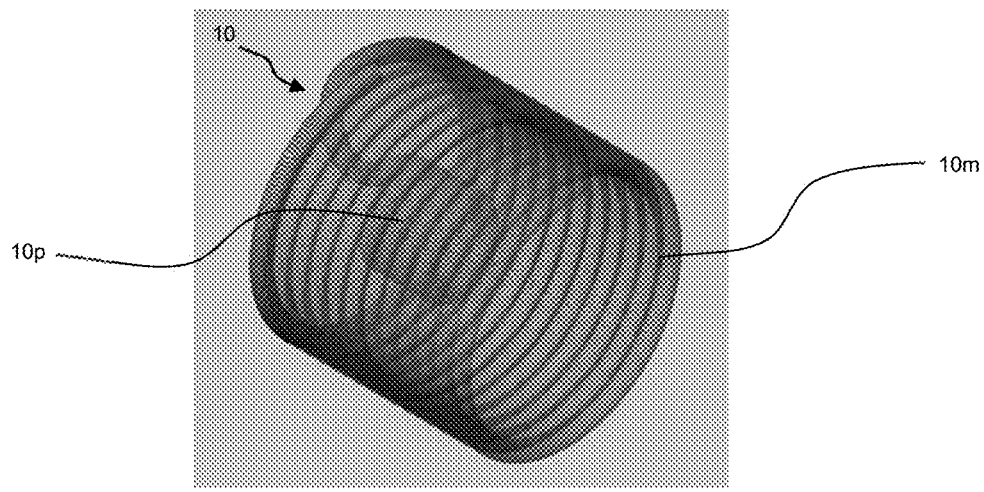

FIG. 3B provides a partially transparent perspective view of an embodiment of an embolic coil with a kick-in tail, in accordance with the present disclosure.

Figure 3C:
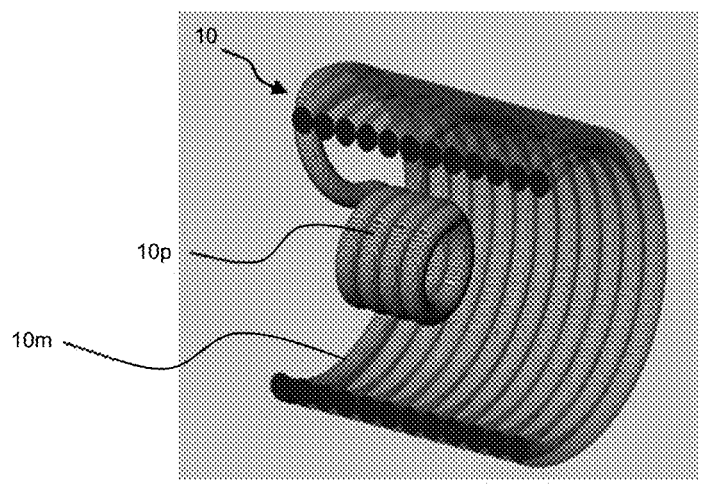

FIG. 3C provides a cutaway perspective view of an embodiment of an embolic coil with a kick-in tail, in accordance with the present disclosure.

FIGS. 4A-D provide perspective views of embodiments of embolic coils with kick-in tails, in accordance with the present disclosure.

Figures 5A, 5B:
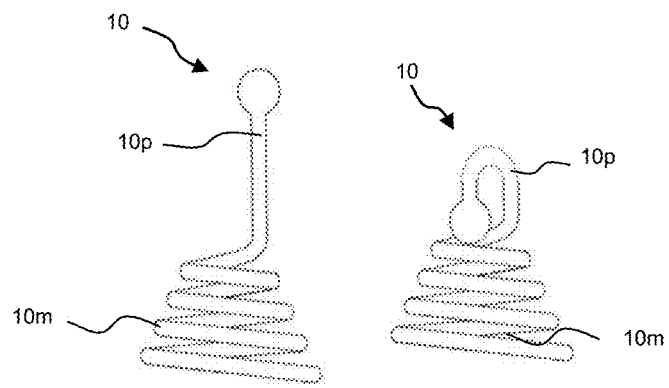

FIG. 5A is a schematic view of a proximal end of an embolic coil without a kick-in tail.

FIG. 5B is a schematic view of a proximal end of an embodiment of an embolic coil with a kick-in tail, in accordance with the present disclosure.

Figure 6A:
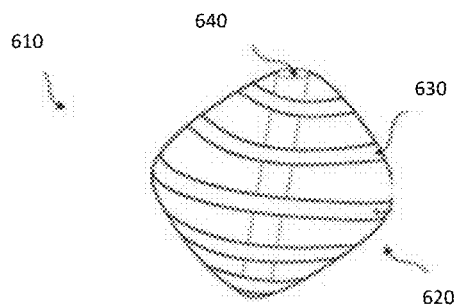

FIG. 6A depicts a side view of a mandrel, in accordance with one embodiment of the present disclosure.

Figure 6B:
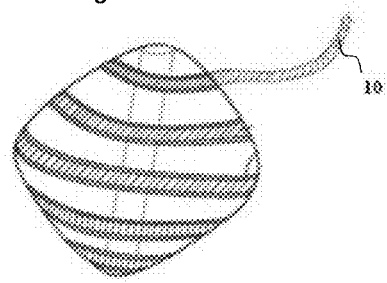
Figure 6C:
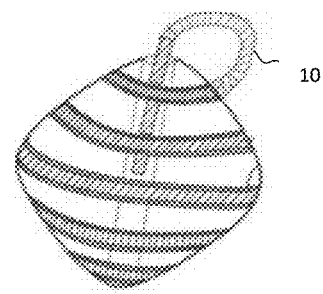

FIGS. 6B-C depict an embodiment of a process for forming an embolic coil with a kick-in tail using the mandrel of FIG. 6A.

Figure 7A:
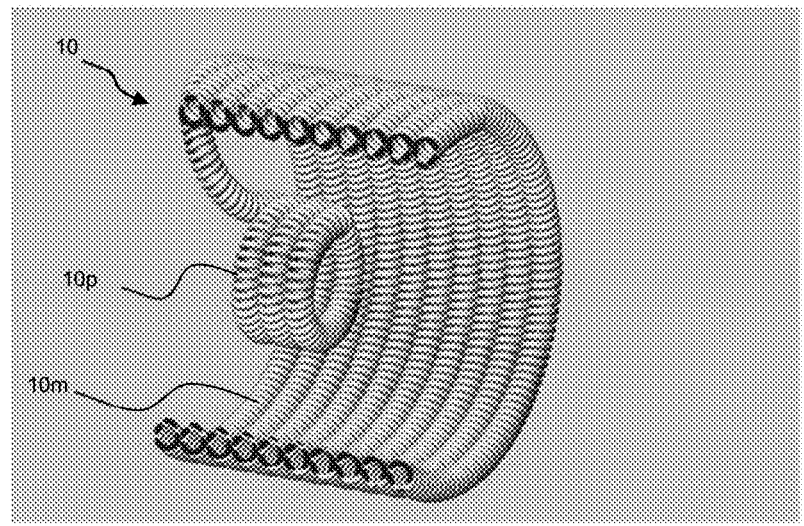

FIG. 7A provides a cutaway perspective view of an embodiment of an embolic coil with a kick-in tail, in accordance with the present disclosure.

Figure 7B:
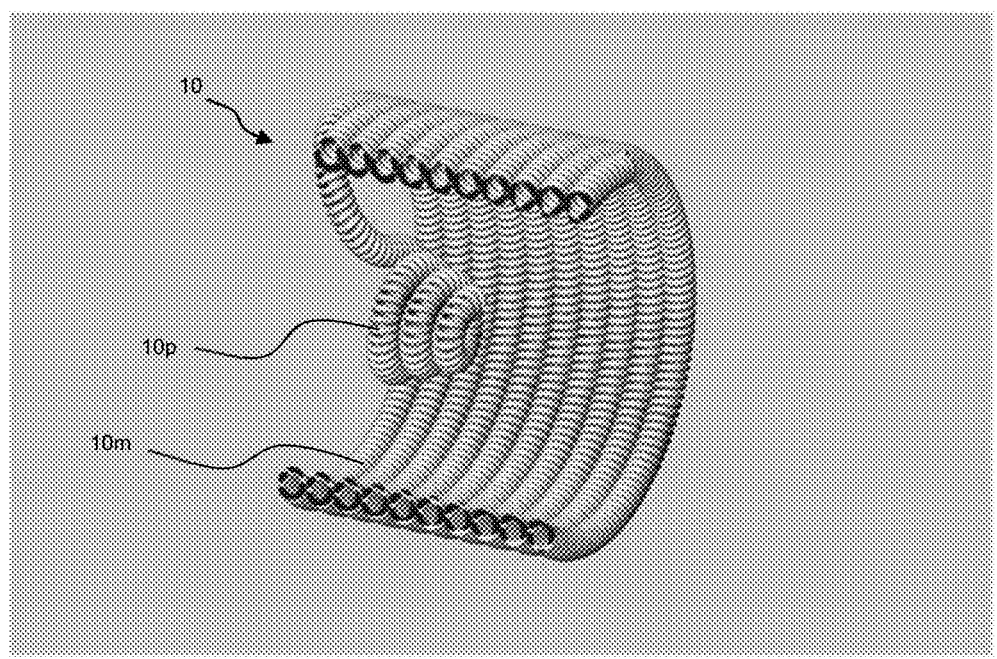

FIG. 7B provides a cutaway perspective view of another embodiment of an embolic coil with a kick-in tail, in accordance with the present disclosure.

DETAILED DESCRIPTION

The present disclosure may be further understood with reference to the following description and the appended drawings, wherein like elements are referred to with the same reference numerals.

The terms "proximal" and "distal" generally refer to the relative position, orientation, or direction of an element or action, from the perspective of a clinician using the medical device, relative to one another. Thus, "proximal" may generally be considered closer to the clinician or an exterior of a patient, and "distal" may generally be considered to be farther away from the clinician, along the length or beyond the end of the medical device.

The present disclosure is related to medical devices used to block the flow of blood through a blood vessel such as, for example, embolic coils.

Embolic coils can generally be used in a number of different applications, such as neurological applications and/or peripheral applications. In some embodiments, embolic coils can be used to occlude a vessel and/or to treat an aneurysm (e.g., an intercranial aneurysm), an arteriovenous malformation (AVM), or a traumatic fistula, among other uses. In some embodiments, embolic coils can be used to embolize a tumor (e.g., a liver tumor). In certain embodiments, embolic coils can be used in transarterial chemoembolization (TACE).

Frequently, an embolic coil is a "coil of a coil." In other words, as used herein, the "primary shape" refers to the configuration obtained when a wire is wound into a coil (i.e., the primary winding). The "secondary shape" refers to the configuration obtained when the primary shape is further shaped, e.g., by winding about a mandrel (i.e., the secondary winding). The "free energy state" refers to the theoretical three-dimensional configuration assumed by the embolic coil as it would exist with no outside forces exerted upon it in the secondary shape (also referred to herein as the "free energy secondary shape"). The "deployed shape" refers to the configuration after the embolic coil has been deployed from the delivery catheter. The deployed shape of a particular embolic coil may differ, depending on whether it is deployed into an open space, or whether it is deployed into a body cavity which may influence the three-dimensional structures. The deployed shape may comprise, for example, overlapping and intertwining loops or ovals of the secondary winding.

Figure 1:
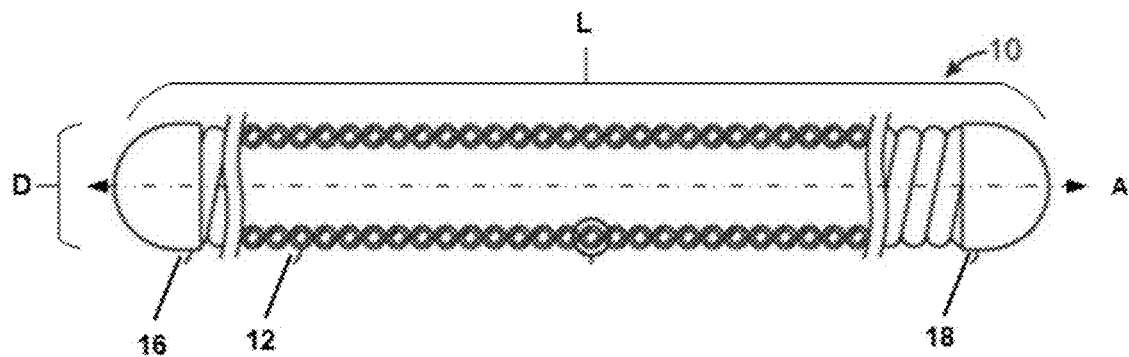
FIG. 1 depicts a primary shape of an embolic coil, in accordance with one embodiment of the present disclosure.

FIG. 1 illustrates a primary shape of an embolic coil 10 with a distal end 18 and proximal end 16 that is formed of consecutive windings of wire 12 and having a primary axis A. It should be noted that the cross-sectional dimension of the wire can be varied depending on the requirements of a particular coil design. For example, the diameter of the wire 12 can be selected, for instance, based on the desired properties (e.g., size, strength) and/or applications of embolic coil 10. In some embodiments, wire 12 can have a diameter of from 0.001 inch (0.025 mm) to 0.005 inch (0.13 mm), among other values.

In some embodiments, the overall diameter D of the primary shape coil may range, for example, from 0.01 inch (0.25 mm) to 0.05 inch (1.3 mm), for instance, ranging from 0.0125 inch (0.32 mm) to 0.025 inch (0.64 mm) or ranging from 0.025 inch (0.64 mm) to 0.045 inch (1.14 mm), among various other possible values.

In some embodiments, the wire 12 has a diameter that is sufficient to provide an embolic coil 10 with a hoop strength capable of holding the embolic coil 10 in place within the chosen body site, lumen or cavity, without substantially distending the wall of the site and without moving from the site as a result of the repetitive fluid pulsing of the vascular system.

In certain embodiments described herein, the overall axial length L of the primary embolic coil 10 may be in the range of 0.5 to 100 cm, and more typically, in the range of 2 to 60 cm. Depending on the use, the embolic coil 10 may have, for example, 10-75 or more turns per centimeter. In other embodiments, the embolic coil 10 can have other lengths and/or numbers of turns per centimeter.

Wire 12 can be formed of, for example, one or more metals or metal alloys, including platinum group metals, particularly platinum, rhodium, palladium, and rhenium, as well as tungsten, gold, silver, tantalum, and alloys of these metals including platinum alloys (e.g., a platinum-tungsten alloy), as well as stainless steel, nickel-titanium alloys (nitinol), and Elgiloy® (from Elgiloy Specialty Metals). In certain embodiments, wire 12 may be formed of one or more polymers. Examples of polymers include polyolefins, polyurethanes, block copolymers, polyethers, and polyimides. Other examples of polymers are disclosed, for example, in Buiser et al., U.S. Patent Pub. No. 2007/0141099, which is incorporated herein by reference.

Coils formed from various metals and alloys including platinum and its alloys, among many others, are known to exhibit elasticity in that they can be deformed under stress and recover to or toward an original or "memorized" shape once the stress is removed (i.e., where the coil is in a free energy state).

Those skilled in the art will also understand that alloys such as Nitinol exhibit what are known as superelasticity effects. That is, when a stress is applied to the alloy element in the austenitic phase, the element deforms. This deformation may generate large areas of strain-induced martensite material even if there is no temperature change. These areas occur primarily at points where the strain is highest and may result in deformations that would be unrecoverable in normal materials. However, at that temperature martensite is not the stable phase of the alloy, and as soon as the stress has been removed the alloy returns to an austenitic state and reverts to its original shape.

Figure 2:
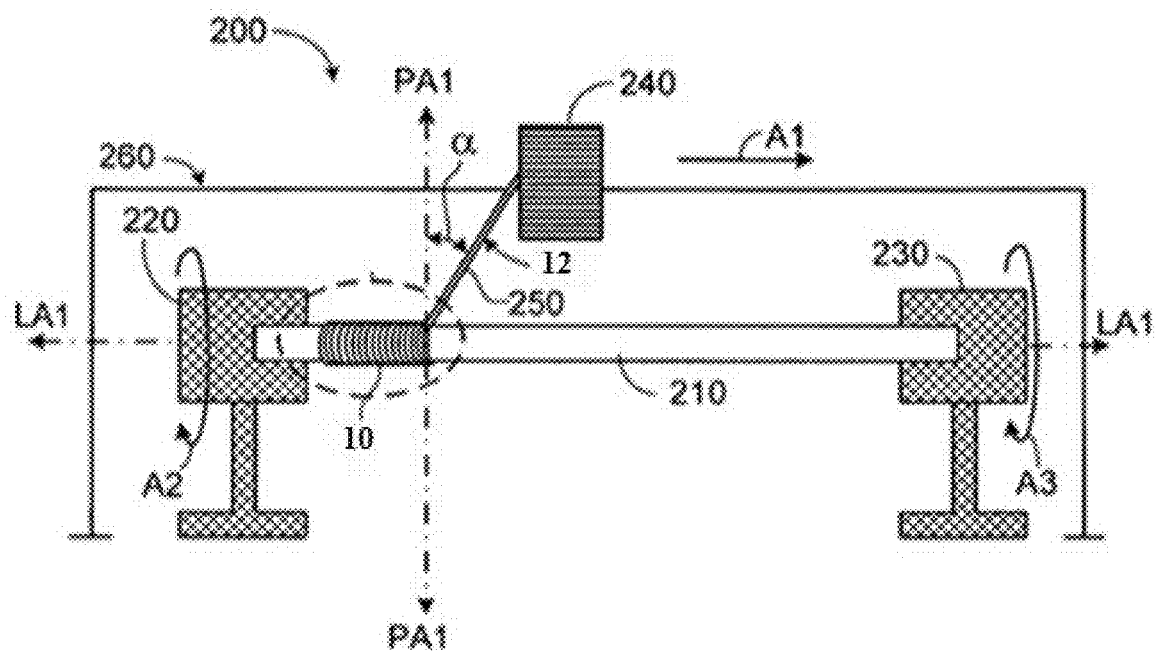
FIG. 2 depicts a side view of an embodiment of a process for forming an embolic coil, in accordance with the present disclosure.

FIG. 2 illustrates one example of a process for forming a coil (e.g., embolic coil 10) in its primary shape. As shown in FIG. 2, a coil-forming apparatus 200 may include a mandrel 210 held by two rotatable chucks 220 and 230. A spool 240 of wire 12 is disposed above mandrel 210, and is attached to a linear drive 260. To form a coil in its primary shape, chucks 220 and 230 are activated so that they rotate in the direction of arrows A2 and A3, thereby rotating mandrel 210. Linear drive 260 is also activated, and moves spool 240 in the direction of arrow A1. The rotation of mandrel 210 pulls wire 12 from spool 240 at a predetermined pull-off angle, and causes wire 12 to wrap around mandrel 210, forming a coil 10.

As FIG. 2 shows, the pull-off angle (a) is the angle between axis PA1, which is perpendicular to longitudinal axis LA1 of mandrel 210, and the portion 250 of wire 12 between spool 240 and coil 10. In some embodiments, angle (a) may be from about one degree to about six degrees, among other values. In certain embodiments, a controller (e.g., a programmable logic controller) can be used to maintain the pull-off angle in coil-forming apparatus 200. Because mandrel 210 is rotating as it is pulling wire 12 from spool 240, and because linear drive 260 is moving spool 240 in the direction of arrow A1, wire 12 forms coil 10 in a primary shape around mandrel 210. Coil 10 can be formed, for example, at room temperature (25° C.). The tension of mandrel 210 as it is held between chucks 220 and 230 may be sufficiently high to avoid vibration of mandrel 210 during the winding process, and sufficiently low to avoid stretching of mandrel 210 during the winding process.

After coil 10 has been formed, chucks 220 and 230, and linear drive 260, are deactivated, and portion 250 of wire 12 is cut. Mandrel 210 may then be released from chuck 220, and coil 10 is pulled off of mandrel 210. In embodiments, coil 10 may have a length of from about five centimeters to about 225 centimeters after being removed from mandrel 210, among other values. After coil 10 has been removed from mandrel 210, coil 10 may be cut into smaller coils, if desired. While coil 10 might lose some of its primary shape as it is pulled off of mandrel 210, coil 10 can generally return to its primary shape shortly thereafter, because of memory imparted to coil 10 during formation. In some embodiments, after coil 10 has been removed from mandrel 210, one or both of the ends of coil 10 can be heated and melted to form rounder, more biocompatible (e.g., atraumatic) ends.

Once coil 10 has been formed in its primary shape, coil 10 can be further shaped into a secondary shape, for example, as discussed below in conjunction with FIGS. 6A-6C.

In general, the embolic coils 10 described herein only exhibit a primary shape when fully extended within the lumen of a delivery catheter. As embolic coil 10 exits the delivery catheter it assumes its secondary shape, which allows embolic coil 10 to fill aneurysmal sac or other structure. Typically, the primary shape of embolic coil 10 is selected for deliverability, and the secondary shape of embolic coil 10 is selected for application (e.g., embolization of an aneurysm).

One exemplary secondary shape in accordance with an embodiment of the present disclosure is illustrated in FIGS. 3A-C, which show various views of an embolic coil 10 with free energy secondary shapes in which a main portion 10m defines a volume, specifically a cylindrical volume, and in which a proximal end 10p is disposed within the volume. Additional secondary shapes in accordance with embodiments of the present disclosure are illustrated in FIGS. 7A and 7B, which show additional cutaway views of embolic coils 10 with free energy secondary shapes in which a main portion 10m defines a volume, specifically a cylindrical volume, and in which a proximal end 10p is disposed within the volume.

Figure 4A:
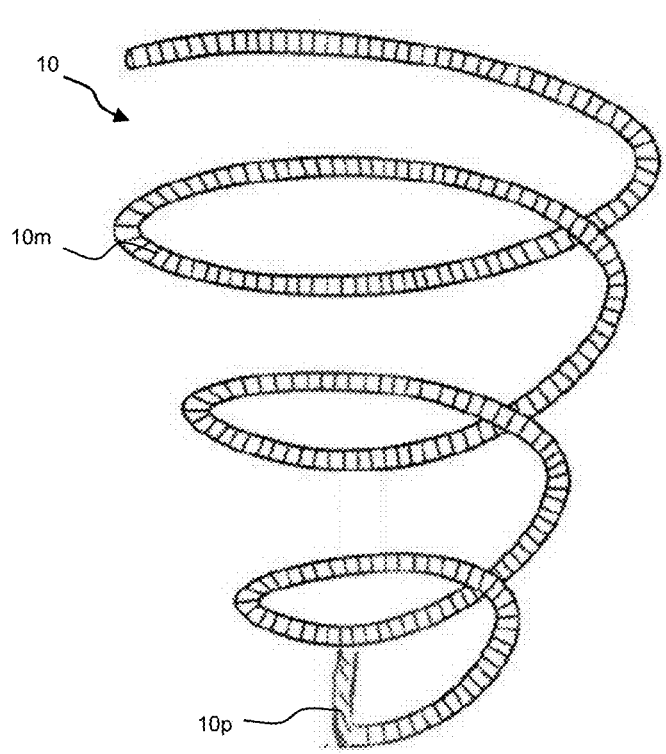
Figure 4B:
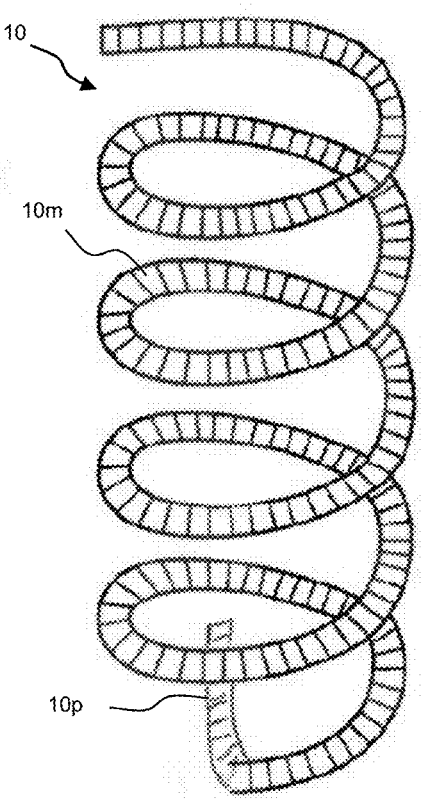
Figure 4C:
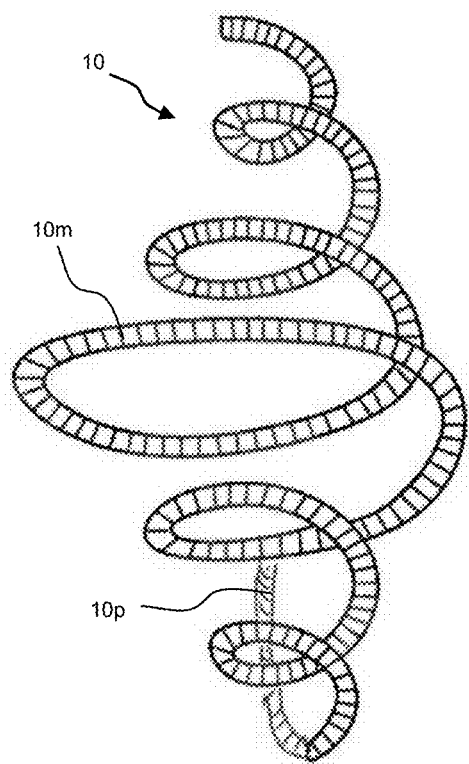

FIGS. 4A-4D, illustrate that other embolic coils may be formed which can have any number of different secondary shapes. In these figures, embolic coils 10 have been formed with free energy secondary shapes in which a main portion 10m defines a volume, specifically a cylindrical volume (FIG. 4B), a conic volume (FIGS. 4A and 4D) and a dual conic volume (FIG. 4C). In each case, the free energy secondary configuration is one in which the proximal end 10p of the coil 10 bends back in the direction or into the volume formed by the coil. In a typical coil, the maximum width of the secondary structure may range from 2 to 50 times the diameter of the primary coil, for example, ranging from 2 to 5 to 10 to 25 to 50 times (i.e., ranging between any two of the preceding numerical values) (e.g., ranging from 2 to 25 times, ranging from 5 to 50 times, ranging from 5 to 25 times, etc.) the diameter of the primary coil.

In embodiments where the secondary shape defines a volume and a proximal end of the primary shape bends back in the direction of or into the volume, the greatest width of the volume may be at least one times the bending radius of the proximal end. For example, the greatest width of the volume may range from 1 to 2.5 to 5 to 10 to 25 to 50 to 100 times (i.e., ranging between any two of the preceding numerical values) (e.g., ranging from 1 to 100 times, ranging from 2.5 to 50 times, ranging from 5 to 25 times, etc.) the bending radius of the proximal end, among other values.

Figure 4D:
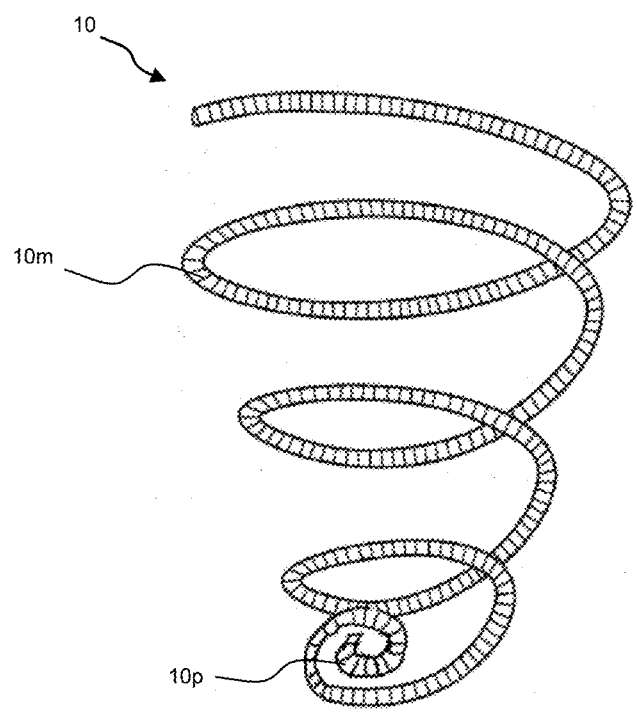

More particularly, FIGS. 3A-3C, 4B, 7A and 7B show embolic coils 10 with a kick-in tail 10p and a generally cylindrical secondary shape, also referred to as a helical shape, which can be used, for example, to provide a supportive framework along a vessel wall. Alternatively, an embolic coil with a cylindrical secondary shape can be used to retain other embolic coils that are subsequently delivered to the target site, among other uses. FIGS. 4A and 4D show embolic coils 10 with a kick-in tail 10p and a conic secondary shape, also known in the art as a single apex vortex secondary shape, which can be used, for example, to close the center of a target site that is to be occluded, and/or to occlude a target site, among other uses. For example, an embolic coil with a single apex vortex secondary shape may be used to occlude a vessel having low flow, intermediate flow, or high flow. In certain embodiments, an embolic coil with a single apex vortex secondary shape can be used as a packing coil, such that the coil can be packed into a vessel that is slightly smaller than the diameter of the coil. In some embodiments, an embolic coil with a single apex vortex secondary shape can be used to embolize a tumor and/or treat gastrointestinal bleeding, among other uses. FIG. 4C shows an embolic coil 10 with a kick-in tail 10p and a dual conic secondary shape, also known in the art as a dual apex vortex secondary shape or a "diamond" secondary shape, which, like the single apex vortex secondary shape, can be used, for example, to close the center of a target site that is to be occluded, and/or to occlude a target site in conjunction with an embolic coil such as helical embolic coil 10 (FIGS. 3A-3C, 4A), among other uses.

FIGS. 5A-B schematically illustrate proximal ends 10p of embolic coils 10 without (FIG. 5A) and with (FIG. 5B) a kick-in tail. As depicted in FIG. 5B, a bend introduced sufficiently close to the proximal end of coil 10 can provide a kick-in tail that points toward, but does not enter, the volume defined by the secondary coil shape. In some embodiments, a bend with a relatively tight radius may be formed, for example, ranging from 0.1 to 25 times the diameter of the coil 10, for example, ranging from 0.1 to 0.25 to 0.5 to 1 to 2.5 to 5 to 10 to 25 times (i.e., ranging between any two of the preceding numerical values) (e.g., ranging from 0.25 to 10 times, ranging from 0.5 to 5 times, ranging from 0.5 to 2.5 times, etc.) the diameter of the coil 10.

As seen from FIGS. 3A-3C, 4D, 7A and 7B, in some embodiments, a bend of more than 180 degrees, for example, ranging from 180 degrees to 270 degrees to 360 degrees to (at which point a loop is formed) to 540 degrees to 720 degrees to 1080 degrees or more (i.e., ranging between any two of the preceding numerical values) (e.g., ranging from 180 degrees to 1080 degrees, ranging from 180 degrees to 720 degrees, ranging from 360 degrees to 1080 degrees, etc.) may be formed (in this regard, FIGS. 3A-3C show a bend of approximately four turns or 1440 degrees, whereas FIGS. 7A and 7B show a bend of approximately three turns or 1080 degrees). FIG. 4D shows an embolic coil 10 with a single apex vortex secondary shape having a kick-in tail that forms a tight two-dimensional spiral. In an analogous embodiment, the kick-in tails provided in FIGS. 3A-3C, 7A and 7B form a tight three-dimensional spiral (e.g., a helix in FIGS. 3A-3C and 7A and a conic spiral in FIG. 7B). In this regard, the embolic coils of FIGS. 3A-3C and 7A have a free energy secondary shape in which a main portion 10m defines a volume, specifically a cylindrical volume defined by a first helix and in which a proximal end 10p is disposed within the volume that comprises a second helix, whereas the embolic coil of FIG. 7B has a free energy secondary shape in which a main portion 10m defines a volume, specifically a cylindrical volume defined by a helix and in which a proximal end 10p is disposed within the volume that comprises a conic spiral. An advantage of such spiral designs is that a kick-in tail may be formed which rolls itself up after being released from a delivery sheath or catheter. As discussed below, such a coil may be made, for example, by disposing a smaller diameter mandrel within a larger diameter mandrel such that the smaller mandrel forms the tail and the larger mandrel forms the secondary shape of the remainder of the coil.

The location of the bend along the length of the proximal end of coil 10 can determine the configuration of the kick-in tail relative to the secondary shape of coil 10. For example, a bend introduced near the proximal end of coil 10 (e.g., 0.5 to 5.0 cm from the proximal end of coil 10) may allow the kick-in tail to fold within the lumen defined by the secondary coil shape (see, e.g., FIGS. 4A-C). However, a bend introduced at a greater length from the proximal end of coil 10 (e.g., 5.0 to 10.0 cm) may result in a kick-in tail disposed outside and adjacent to the secondary coil shape (see, e.g., FIG. 4C). This occurs due to the steric hindrance of the secondary coil shape, which begins to form prior to the proximal portion of coil 10 exiting the delivery catheter, physically blocking the kick-in tail from entering the lumen defined by the final coil shape.

Various methods for forming secondary shapes for the embolic coils described herein will now be described. Once coil 10 has been formed in its primary shape (see FIGS. 1-2), coil 10 can be further shaped into a secondary shape using a suitable mandrel or mandrels.

FIG. 6A shows a mandrel 610 which may be used to form a secondary shape of coil 10. While mandrel 610 is shaped to form a "diamond-shaped" coil, other types of mandrels can be used to form other secondary shapes. Mandrel 610 comprises a "diamond-shaped" block 620 with grooves 630 cut into its surface, and an aperture 640 (e.g., a channel) extending at least partially therethrough. As shown in FIGS. 6B and 6C, coil 10 in its primary shape may be wrapped around mandrel 610, such that coil 10 fills grooves 630, creating the secondary shape. The ends of coil 10 are fixed to mandrel 610. In accordance with an embodiment of the present disclosure, one end of the primary coil 10, specifically the proximal end of the deliverable coil is inserted into the aperture 640 as shown in FIG. 6C. The coil 10 is heat-treated at a temperature and for a time sufficient to set or program the coil in a three-dimensional secondary shape, thereby imparting memory to the coil 10. After being heat-treated, coil 10 is unwrapped from mandrel 610. The removal of coil 10 from mandrel 610 allows coil 10 to reassume its secondary shape. In some embodiments, after coil 10 has been removed from mandrel 610, one or both of the ends of coil 10 can be heated and melted to form rounder, more biocompatible (e.g., atraumatic) ends.

In one embodiment, the configuration of the kick-in tail relative to the secondary shape of coil 10 is determined by the (a) extent (i.e., degree) to which the proximal end of the coil 10 is bent during the wrapping of coil 10 around mandrel 610 and, (b) the location at which the bend is introduced along the proximal end of coil 10. For example, with regard to extent, a bend of at least 90 degrees, in some embodiments, at least 180 degrees, at least 270 degrees, at least 360 degrees (at which point a loop is formed), for instance ranging anywhere from 90 to 720 degrees or more can be introduced into the proximal end of the coil 10. In the embodiment shown, the bend angle is determined by the amount of slack that is provided before the proximal end of the coil 10 is inserted into the aperture 640 of mandrel 610. As used herein, "slack" refers to the portion of coil 10 that is not wound around mandrel 610. For example, a sharp angle can be obtained by inserting coil 10 directly into aperture 640 as the coil 10 comes off mandrel 610. Similarly, a more gradual angle can be achieved by leaving a slack portion at a point where the proximal end of coil 10 into aperture 640.

In the embodiment shown in FIGS. 6A-6C, the aperture 640 corresponds to a linear channel that is disposed at a 90 degree angle relative to the surface. In other embodiments the aperture is disposed at a lesser angle. In some embodiments, the aperture 640 may be made non-linear in order to form a distal tip having a desired shape. For example, a non-linear aperture 640 may be formed which meets the mandrel surface at an angle that is substantially less the 90 degrees and which gradually curves away from the surface.

In another embodiment, the proximal end of coil 10 that is not wound around mandrel 610 can be formed into a tight curl (i.e., rolled up) prior to being disposed within an aperture or hollow volume of the mandrel. When in the secondary shape, this embodiment would provide a coil 10 with a kick-in tail having a two-dimensional spiral shape (e.g., a watch-spring shape) or a three-dimensional shape (e.g., a helical or corkscrew shape), depending on how the proximal end is curled.

In this regard, more complex coil designs such as that shown in FIGS. 3A-3C may be formed by disposing a smaller mandrel within a larger hollow mandrel. For instance, a primary coil may be wrapped around a larger cylindrical mandrel as well as a smaller cylindrical mandrel which is disposed within a hollow volume of the larger cylindrical mandrel, in order to form the coil of FIGS. 3A-3C.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. Certain embodiments of the present disclosure have described above. It is, however, expressly noted that the present disclosure is not limited to those embodiments, but rather the intention is that additions and modifications to what was expressly described herein are also included within the scope of the disclosure. Moreover, it is to be understood that the features of the various embodiments described herein were not mutually exclusive and can exist in various combinations and permutations, even if such combinations or permutations were not made express herein, without departing from the spirit and scope of the disclosure. In fact, variations, modifications, and other implementations of what was described herein will occur to those of ordinary skill in the art without departing from the spirit and the scope of the disclosure. As such, the disclosure is not to be defined only by the preceding illustrative description.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An embolic coil comprising:
   an elongate helical primary shape having a diameter, a first end, a second end, and defining a lumen there along having a volume;
   a bend in the first end of the primary shape extending into the volume; and
   a secondary shape defining a helix and a terminal end, wherein the entire helix and the terminal end are contained between the bend and the second end.

2. The embolic coil of claim 1, wherein a bending radius of the bend is less than five times the diameter of the elongate helical primary shape when the coil is in the free energy state.

3. The embolic coil of claim 1, wherein the first end bends at an angle greater than 360 degrees when the coil is in the free energy state.

4. The embolic coil of claim 1, wherein the first end comprises a two-dimensional spiral or a three-dimensional spiral when the coil is in the free energy state.

5. The embolic coil of claim 1, wherein the bend points toward the second end.

6. The embolic coil of claim 1, wherein the secondary shape defines a lumen therethrough, and wherein the first end of the primary shape is at least partially disposed within the lumen of the primary shape when the coil is in the free energy state.

7. The embolic coil of claim 6, wherein the secondary shape is substantially in the form of a cylinder which forms the lumen of the secondary shape when the coil is in the free energy state.

8. The embolic coil of claim 1, wherein the bend is such that a tip of the first end points into the volume when the coil is in the free energy state.

9. The embolic coil of claim 8, wherein the first end bends at an angle greater than 60 degrees and less than 225 degrees when the coil is in the free energy state.

10. The embolic coil of claim 8, wherein the secondary shape has a secondary axis and wherein an axis of the primary shape at a tip of the first end is within 45 degrees of parallel to the secondary axis when the coil is in the free energy state.

11. The embolic coil of claim 1, wherein the volume is a single conic volume, a dual conic volume, or a cylindrical volume.

12. The embolic coil of claim 1, wherein the first end is provided with an attachment feature.

13. A delivery sheath containing an embolic coil in accordance with claim 1.

14. A delivery system comprising (a) an embolic coil in accordance with claim 1 and (b) a delivery wire that is temporarily attached to the embolic coil via an attachment feature.

15. The delivery systems of claim 14, wherein the embolic coil comprises a first attachment member that is temporarily interlocked with a second attachment member on the delivery wire.

16. A method comprising:
   (a) advancing an embolic coil of a delivery system to a target occlusion area in a patient, said delivery system comprising:
      (i) an embolic coil comprising:
         an elongate helical primary shape having a diameter, a first end, a second end, and defining a lumen therealong having a volume;
         a bend in the first end of the primary shape extending into the volume; and
         a secondary shape defining a helix and a terminal end, wherein the entire helix and the terminal end are contained between the bend and the second end; and
      (ii) a delivery wire; and
   (b) releasing the embolic coil from the delivery system.

17. The method of claim 16, wherein the embolic coil and delivery wire are loaded into a sheath and wherein the embolic coil is pushed from the sheath using the delivery wire to release the embolic coil.

* * * * *